US007012242B2

(12) United States Patent
Tarozzi et al.

(10) Patent No.: US 7,012,242 B2
(45) Date of Patent: Mar. 14, 2006

(54) METHOD FOR OPTOELECTRONICALLY INSPECTING PHARMACEUTICAL ARTICLES

(75) Inventors: Giorgio Tarozzi, Nonantola (IT); Riccardo Rivalta, Imola (IT); Roberto Trebbi, Castenaso (IT); Pierantonio Ragazzini, Forli' Cesena (IT)

(73) Assignee: I.M.A. Industria Macchine Automatiche S.p.A., Bologna (IT)

( * ) Notice: Subject to any disclaimer, the term of this patent is extended or adjusted under 35 U.S.C. 154(b) by 0 days.

(21) Appl. No.: 10/487,228

(22) PCT Filed: Jun. 27, 2003

(86) PCT No.: PCT/IB03/02976

§ 371 (c)(1),
(2), (4) Date: Feb. 25, 2004

(87) PCT Pub. No.: WO2004/004626

PCT Pub. Date: Jan. 15, 2004

(65) Prior Publication Data

US 2005/0007588 A1     Jan. 13, 2005

(30) Foreign Application Priority Data

Jul. 4, 2002    (IT) .......................... BO2002A0433

(51) Int. Cl.
*B07C 5/344* (2006.01)
*G01V 8/00* (2006.01)

(52) U.S. Cl. .............................. 250/222.1; 250/223 B; 250/559.13; 250/559.4; 209/579; 356/427

(58) Field of Classification Search ................ 250/221, 250/222.1, 222.2, 223 R, 223 B, 559.12, 250/559.13, 559.2, 559.4; 209/524, 576, 209/577, 579; 356/427, 239.5
See application file for complete search history.

(56) References Cited

U.S. PATENT DOCUMENTS

| 3,757,943 A | 9/1973 | Chae et al. |
| 4,028,553 A | 6/1977 | Farcinade |
| 4,182,451 A | 1/1980 | Watson |

FOREIGN PATENT DOCUMENTS

| EP | 0 303 175 | 2/1989 |
| JP | 401086043 A | * 3/1989 |

OTHER PUBLICATIONS

Abstract Only, JP 56 086341, Sep. 29, 1981, Tetsuji Kawasaki.

* cited by examiner

*Primary Examiner*—Kevin Pyo
(74) *Attorney, Agent, or Firm*—Arent Fox PLLC

(57) ABSTRACT

In a method for optoelectronically inspecting pharmaceutical capsules (2) in a capsule filling machine (1), the pharmaceutical capsules (2) are fed in single file from a station (3) where the capsules (2) are made to a capsule (2) outfeed portion (8) of the machine (1) along a defined feed path (P) passing through an inspection station (13). In the inspection station (13), each pharmaceutical capsule (2) passes through an electromagnetic field created by coherent, polarised light radiation.

9 Claims, 2 Drawing Sheets

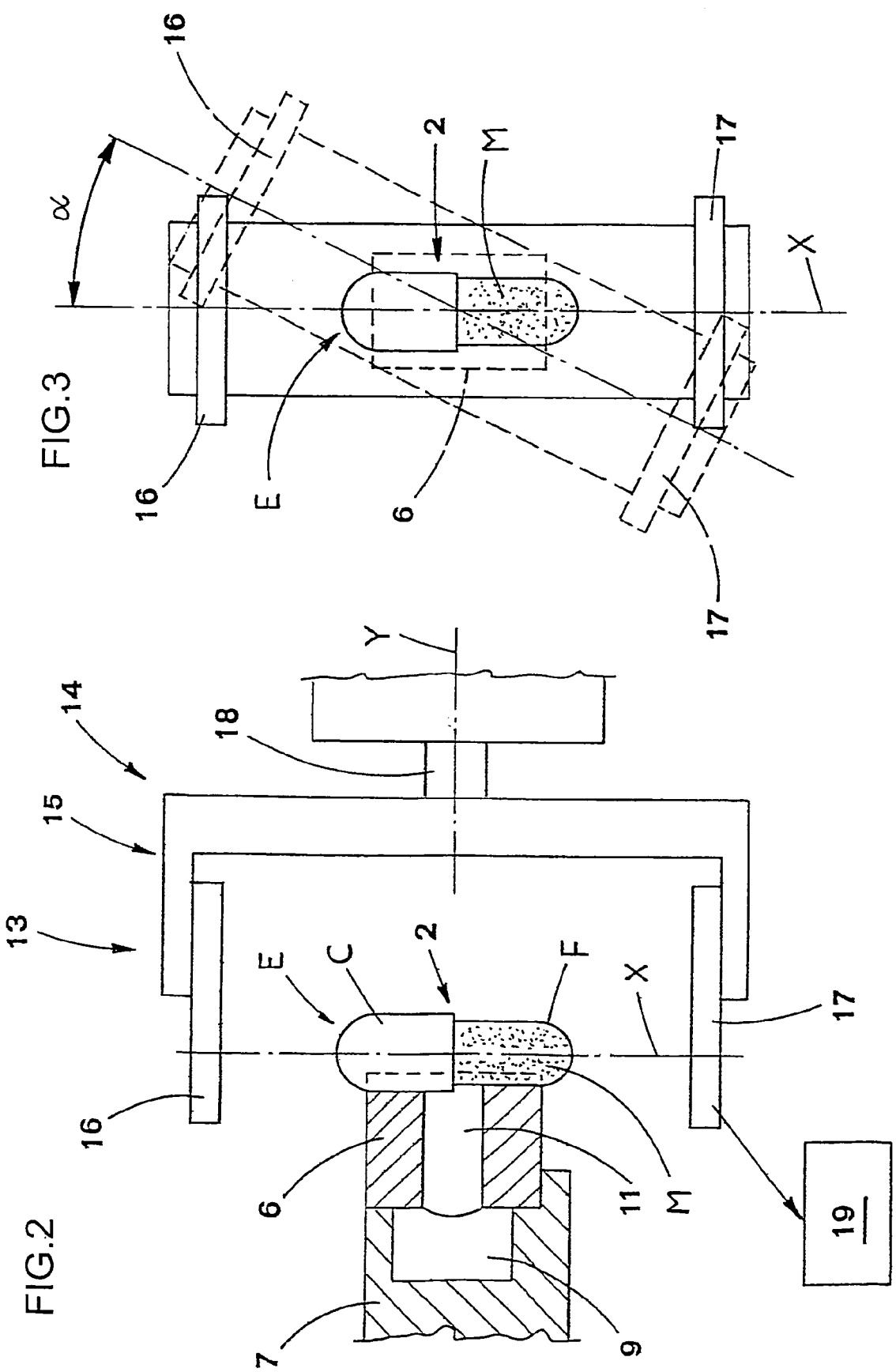

METHOD FOR OPTOELECTRONICALLY INSPECTING PHARMACEUTICAL ARTICLES

CROSS-REFERENCE TO RELATED APPLICATION

This application is a National Stage entry of International Application No. PCT/IB2003/002976, the entire specification claims and drawings of which are incorporated herewith by reference.

TECHNICAL FIELD

The present invention relates to a method for optoelectronically inspecting pharmaceutical articles.

In particular, the present invention can be advantageously applied to capsule filling machines for making hard gelatin capsules of the type with lid and body, filled with doses of pharmaceutical material in powder or particulate form, which the present specification expressly refers to but without restricting the scope of the invention, in order to check defined properties of the capsules through an optoelectronic inspection.

DISCLOSURE OF THE INVENTION

The invention provides a method for optoelectronically inspecting pharmaceutical articles in a machine that makes the articles, characterised in that the pharmaceutical articles are fed in single file from a station where the articles are made to an outfeed station of the articles themselves along a defined feed path passing through an inspection station; each pharmaceutical article passing through an electromagnetic field. Treated by coherent, polarised light radiation in the inspection station.

Preferably, the electromagnetic field is produced by a laser beam source and the articles comprise hard gelatin capsules of the type with lid and body containing doses of pharmaceutical material in powder or particulate form, the machine that makes the articles comprising a capsule filling machine that makes the pharmaceutical capsules; the crossing of the electromagnetic field permitting detection of the level to which the capsules are filled with the pharmaceutical material.

DESCRIPTION OF THE DRAWINGS

The invention will now be described with reference to the accompanying drawings which illustrate a preferred, non-restricting embodiment of a unit, implementing the method according to the invention, for optoelectronically inspecting pharmaceutical articles, and in which:

FIG. 2 is a schematic front view, and a cross section through line II—II, of a detail of the unit of FIG. 1; and FIG. 3 is a side view in cross section of the same detail as that shown in FIG. 2.

DETAILED DESCRIPTION OF THE PREFERRED EMBODIMENTS OF THE INVENTION

Figure 1:
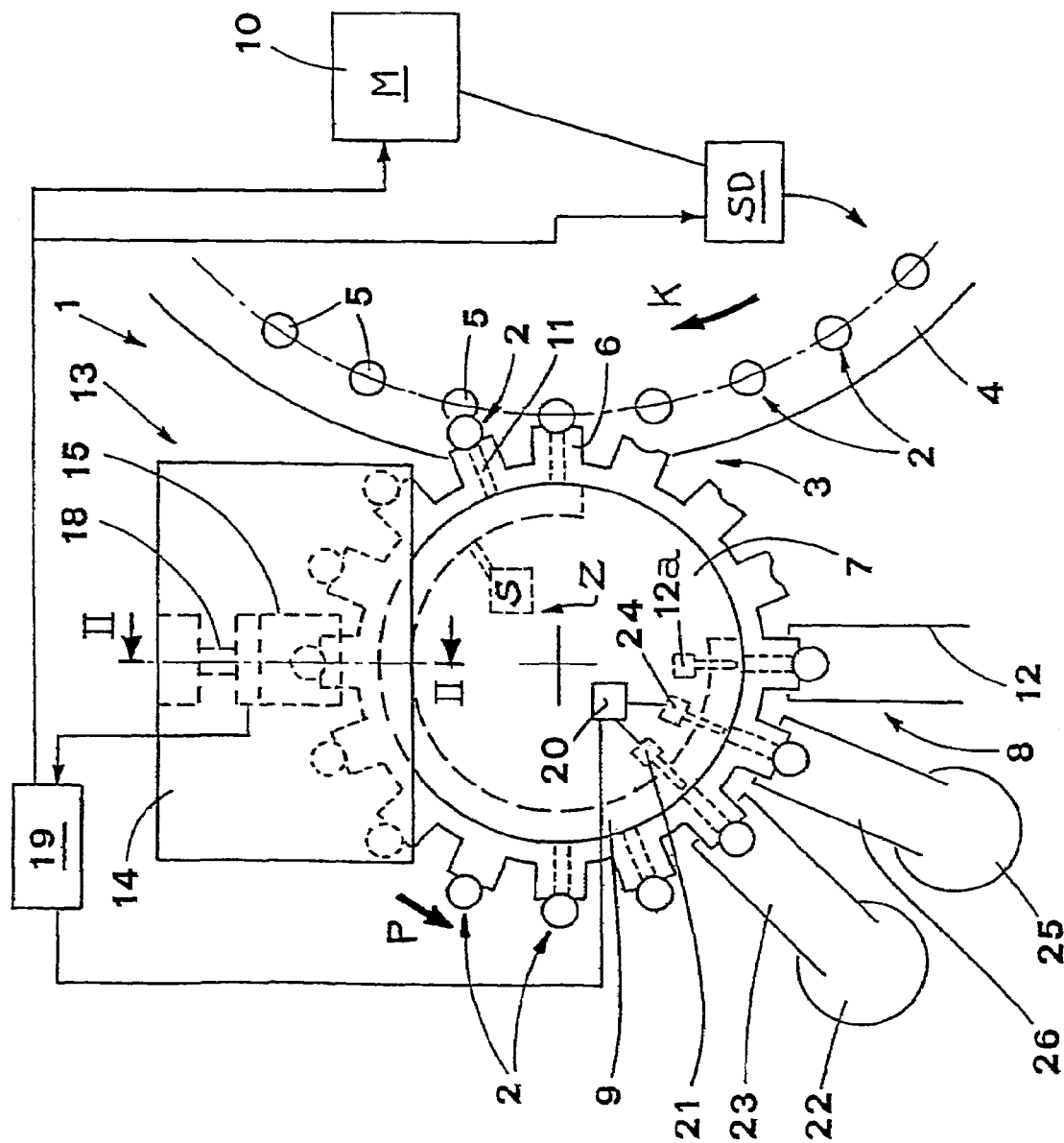
FIG. 1 is a schematic plan view, partly in cross section and with some parts cut away for clarity, of a machine equipped with an operating unit implementing the method according to the invention.

With reference to FIGS. 1 and 2, the numeral 1 denotes in its entirety a machine for filling hard gelatin capsules of known type, each having a lid C and a body F, with doses of pharmaceutical material M, in particular pharmaceutical material M in powder or particulate form, such as, for example, microtablets or pellets. The capsule filling machine 1 is of well known type and basically comprises a station 3 for making the capsules 2, the station 3 in turn comprising a drum 4 that rotates, preferably with continuous motion, in the direction indicated by the arrow K in FIG. 1, and being equipped on its periphery with a set of seats or bushes 5 for accommodating the capsules 2 once closed and filled with the material M.

The material M is fed to the drum 4 in a known manner, which is not illustrated, through a central hopper 10 containing the material M which is dosed into the capsules 2 through a dosing system SD of the type, disclosed for example, in Italian Patent IT 1304779, with pistons that move inside respective cylindrical dosing chambers.

In the bushes 5 of the drum 4, each capsule 2 is set in a vertical position, that is to say, with its longitudinal axis X positioned vertically and with the lid C at the top and the body F below.

From the drum 4, each capsule 2 is ejected in succession from a respective bush 5, by customary expulsion means, which are not illustrated, and, at the station 3, is transferred to a radial seat 6 on a starwheel conveyor 7 that rotates in synchrony with the drum 4 in the direction Z of FIG. 1 opposite the direction of rotation K of the drum 4.

As illustrated in FIG. 1, the conveyor 7 is designed to feed the capsules 2 in succession from a station 3 to an outfeed portion 8 of the machine 1 along a semicircular feed path P, each capsule 2 being held in the vertical position in the respective seat 6 by suction created inside a suction chamber 9 connected to a vacuum source S and to each seat 6 through a respective conduit 11. The outfeed portion 8 comprises a capsule 2 conveyor channel 12 and a nozzle 12a connected to a source of air under pressure (not illustrated) to expel the capsules 2 from the conveyor channel 12, the latter being connected in a known manner which is not illustrated, into an infeed hopper of a packaging machine, for example a blister packer or a machine for filling phials with the capsules 2.

FIG. 1 also shows that between the station 3 and the outfeed portion 8, the path P passes through a station 13 for inspecting the capsules 2.

As illustrated in FIGS. 1 and 2, the inspection station 13 comprises a covering structure 14 defined by an anodised obscure chamber enclosing a unit 15 for supporting the source 16 of a laser beam, that is to say, a beam of high-frequency monochromatic coherent polarised light, which is diffused inside the structure 14 on each capsule 2 held in a respective seat 6, the light then being intercepted by an optical sensor 17 of known CCD matrix type mounted on the side of the unit 15 opposite the laser source 16.

From an operational point of view, optimum results are obtained using laser beam sources of the He Ne type at 623 nanometres with focal spot 0.8 millimetres in diameter, or of the diode type at 650 nanometres with focal spot 2 millimetres in diameter.

More specifically, as each capsule 2 passes through the inspection station 13 supported by the seat 6 of the starwheel conveyor 7, with its axis X perfectly vertical, it enters the structure 14 and crosses the electromagnetic field E created by the laser beam, which checks that it contains a dose of material M and that the material M fills it to the correct level.

As shown in FIG. 3, the unit 15 is mounted on a shaft 18 which is rotationally driven by a customary motor (not illustrated) about a horizontal axis Y, and, during use, is designed to be turned through a defined angle α relative to the axis X so that the level of the material M inside the capsule 2 can be optoelectronically checked from different angles.

Preferably, the angle α is varied from 0 to 30°.

The station 13 also comprises a monitoring device 19 that is connected to the sensor 17 and that is designed to receive from the sensor 17 a signal relating to the measured level of material M with which each capsule 2 is filled, to compare this measured value with a preset reference value, and to generate an output signal that activates a device 20 for rejecting any capsules 2 that do not conform with the reference value.

As illustrated in FIG. 1, the rejection device 20 comprises a first nozzle 21, which is connected in a known manner that is not illustrated to a source of air under pressure and which, on receiving a control signal from the monitoring device 19, issues a jet of air which, by overcoming the suction in the seats 6, diverts from the path P individual non-conforming capsules 2, causing them to be expelled and fed out through a conveyor channel 23 leading into a rejection container 22.

The monitoring device 19 is also connected to the machine 1 system SD which doses the pharmaceutical material M so that, if a significant average percentage of the checked capsules 2 are found to be unsatisfactory, the device 19 sends a feedback signal to the dosing system SD in order to automatically adjust the material M dosing parameters of the machine 1.

Again with reference to FIG. 1, the rejection device 20 also comprises a second nozzle 24, which is connected in a known manner that is not illustrated to the source of air under pressure and which, on receiving a control signal from the monitoring device 19, issues a jet of air which diverts from the path P a specified number of sample capsules 2, causing them to be expelled and fed out through a conveyor channel 26 leading into a rejection container 25.

Advantageously, the sample capsules 2 collected in the container 25 can be weighed on analytical precision balances and the weights thus measured, from which the material M filling levels can be calculated, are transferred to the memory medium of a personal computer and compared with the filling levels measured by the monitoring device 19 to check for significant deviations between the two sets of values.

Thus, the unit 14 can be periodically tested for working efficiency and when deviations are found in a significant average number of samples, the system SD for dosing the material M in the capsule filling machine 1 can be adjusted accordingly.

To conclude, it is evident that the method can be used to optimally and automatically inspect, by electronic means within the machine 1, all the capsules 2 made by the machine 1 itself to check that they have been filled to the right level. Furthermore, the filling level of only a specified quantity of sample capsules 2 can also be checked.

What is claimed is:

1. A method for optoelectronically inspecting pharmaceutical articles in a machine that makes the articles, characterised in that the pharmaceutical articles are fed in single file from a station where the articles are made to an outfeed portion of the machine along a defined feed path passing through an inspection station; each pharmaceutical article, as it travels through the inspection station, passing through an electromagnetic field created by coherent polarised light.

2. The method according to claim 1, characterised in that the electromagnetic field is created by a laser beam source.

3. The method according to claim 1, characterised in that the articles comprise hard gelatin capsules of the type with lid and body containing doses of pharmaceutical material in powder or particulate form, and in that the machine comprises a capsule filling machine that makes the pharmaceutical capsules; the crossing of the electromagnetic field permitting detection that the capsules have been filled with doses of material.

4. The method according to one of claims 2 or 3, characterised in that the electromagnetic field is created inside a structure which is located in the inspection station and which encloses a unit for supporting the laser beam source and, on the opposite side, optical sensor means designed to intercept the laser beam; each capsule crossing electromagnetic field between the laser beam, source and the optical sensor means being held by suction in a seat of a rotary conveyor with suction seats.

5. The method according to claim 4, characterised in that the supporting unit is mounted on a shaft that rotates about a horizontal axis and in that each capsule is held on the respective seat with its longitudinal axis positioned vertically; the method comprising the step of turning the unit through a defined angle relative to the longitudinal vertical axis of the capsule.

6. The method according to claim 5, characterised in that the unit is turned through an angle ranging from 0° to 30°.

7. The method according to claim 4, characterised in that it comprises a monitoring device connected to the optical sensor means; the method comprising the step of the monitoring device receiving a measured value from the optical sensor means, comparing this measured value with a preset reference value, and sending an output signal that activates a device for rejecting the articles that do not conform with the reference value.

8. The method according to claim 7, characterised in that the rejection device is located upstream of the outfeed portion on the path; the non-conforming capsules being diverted from the path by pneumatic deflecting means, causing them to be expelled into a rejection container.

9. The method according to claim 7, characterised in that the monitoring device is connected to a unit for feeding and dosing the pharmaceutical material in the capsule filling machine; the method comprising the step of the monitoring device sending a feedback adjustment signal to the feed and dosing unit.

* * * * *